United States Patent
Schmechel

(10) Patent No.: US 10,793,620 B2
(45) Date of Patent: Oct. 6, 2020

(54) METHOD FOR PRODUCING ANTIGEN-SPECIFIC B CELLS AND THEIR USE FOR THE PRODUCTION OF HYBRIDOMA CELLS AND MONOCLONAL ANTIBODIES

(71) Applicant: BioGenes GmbH, Berlin (DE)

(72) Inventor: Detlef Schmechel, Berlin (DE)

(73) Assignee: BIOGENES GMBH, Berlin (DE)

( * ) Notice: Subject to any disclaimer, the term of this patent is extended or adjusted under 35 U.S.C. 154(b) by 169 days.

(21) Appl. No.: 15/486,360

(22) Filed: Apr. 13, 2017

(65) Prior Publication Data
US 2017/0298116 A1    Oct. 19, 2017

(30) Foreign Application Priority Data
Apr. 14, 2016   (EP) ..................................... 16165226

(51) Int. Cl.
| | |
|---|---|
| *C12N 5/12* | (2006.01) |
| *C07K 16/00* | (2006.01) |
| *C12N 5/0781* | (2010.01) |
| *A01K 67/027* | (2006.01) |
| *C12N 5/16* | (2006.01) |
| *A61K 39/00* | (2006.01) |

(52) U.S. Cl.
CPC .......... *C07K 16/00* (2013.01); *A01K 67/0271* (2013.01); *C12N 5/0635* (2013.01); *C12N 5/163* (2013.01); *A01K 2207/12* (2013.01); *A61K 2039/5158* (2013.01); *A61K 2039/6031* (2013.01); *C07K 2317/10* (2013.01); *C07K 2317/14* (2013.01); *C07K 2317/20* (2013.01)

(58) Field of Classification Search
None
See application file for complete search history.

(56) References Cited

U.S. PATENT DOCUMENTS

2015/0087065 A1 *  3/2015  Haecker ............... C12N 5/0645
                                                                  435/455

FOREIGN PATENT DOCUMENTS

| WO | WO9717446 | * | 5/1996 |
| WO | 9912553 | | 3/1999 |
| WO | 2015117162 | | 8/2015 |

OTHER PUBLICATIONS

Yefenof et al ( J of Immunol. 1985, v.135, pp. 3777-3784.*
Klaus G G et al: "Interaction of B cells with activated T cells reduces the threshold for CD40-mediated B cell activation.", U.S. National Library of Medicine (NLM), Bethesda, MD, US; Jan. 1999 (Jan. 1999). Abstract only.
Sethi K K et al: "Generation of hybridoma cell lines producing monoclonal antibodies against Toxoplasma gondii or rabies virus following fusion of in in vitro-immunized spleen cells with myeloma cells", Annales De L'Institut Pasteur. Immunologie, Elsevier, Paris, FR, vol. 132, No. 1, Jan. 1, 1981 (Jan. 1, 1981), pp. 29-41.
European Search Report completed on Oct. 19, 2016 from EP 16165226.

* cited by examiner

*Primary Examiner* — Michail A Belyavskyi
(74) *Attorney, Agent, or Firm* — Fox Rothschild, LLP; Gregory A. Nelson; Amy A. Dobbelaere

(57) ABSTRACT

The invention refers to a non-therapeutic method for producing antigen-specific B cells by using the adoptive cell transfer of primed B cells, especially of spleen cells including B cells of a previously immunized non-human animal and by administering an antigen of interest to a naïve non-human animal.

12 Claims, No Drawings

METHOD FOR PRODUCING ANTIGEN-SPECIFIC B CELLS AND THEIR USE FOR THE PRODUCTION OF HYBRIDOMA CELLS AND MONOCLONAL ANTIBODIES

CROSS REFERENCE TO RELATED APPLICATIONS

This U.S. application claims priority to European Application No.: 16165226.8 filed Apr. 14, 2016, entitled "A method for producing antigen-specific B cells and their use for the production of hybridoma cells and monoclonal antibodies" the entirety of which is incorporated herein by reference.

The invention refers to a non-therapeutic method for producing antigen-specific B cells by using the adoptive cell transfer of primed B cells, especially of spleen cells including B cells of a previously immunized non-human animal and by administering an antigen of interest to a naïve non-human animal. These primed B cells (for transfer) as well as the (de novo) antigen-activated B cells of the immunized animal (recipient's own B cells) are isolated from a non-human animal immunized with the antigen of interest. The antigen-specific B cells produced are able to provide monoclonal antibodies by using the well-known hybridoma technology. Hybridoma cells and monoclonal antibodies produced using the antigen-specific B cells are also subject matter of the present invention.

A strong antibody response in a host animal is induced by activating antigen-reactive B cells and their terminal differentiation into antibody-secreting plasma cells. This activation and differentiation process is highly influenced by the immunogenicity of the antigen and the efficient cellular collaboration between B cells and helper T cells. Because of their ability to bind selectively to an antigen of interest, antibodies have been used widely for research, diagnostic and therapeutic applications. The potential use of antibodies was expanded with the development of monoclonal antibodies. In contrast to polyclonal antiserum, which comprises a mixture of antibodies directed against multiple epitopes, monoclonal antibodies are directed against a single determinant or epitope on the antigen and are homogeneous. Moreover, monoclonal antibodies can be produced in unlimited quantities. Köhler's and Milstein's seminal work [Köhler and Milstein *Nature* 256:495 (1975)] describes the original method for obtaining hybridoma cells that can produce monoclonal antibodies. An antibody-secreting cell, isolated from an immunized mouse, is fused with a myeloma cell, a type of cancerous B cell. The resulting hybrid cells (hybridomas) are immortal and continuously secrete specific antibodies with reproducible characteristics.

The success of the original hybridoma technique based on cell fusion very much depends on a strong cellular immune response in the spleen at the time of spleen removal for hybridoma production. As this technique uses a whole spleen cell suspension and because all cell types are similarly immortalized by cell fusion, it is critical that the proportion of antigen-specific B cells in the total cell population in the spleen cell suspension is as high as possible. The more specific B cells are present at the time of cell fusion, the higher the chances are of generating target antigen-specific hybridomas.

Typically, the decision to proceed to hybridoma generation depends on reaching a predetermined titer following mouse immunization with a given target antigen. Any titer may be due to the presence of a relatively low number of high affinity/avidity antibodies or the presence of high numbers of relatively low affinity/avidity antibodies. After reaching the specified titer, the appropriate mice are selected for hybridoma generation. Typically, 3-4 days before the scheduled cell fusion, the selected mice are finally boosted with antigen and the spleen is removed and processed on the day of hybridoma generation. However, if the antigen-specific antibody titers at the time of the final boost are still very high, the injected antigen and pre-existing antibodies may immediately form soluble complexes which are cleared by the reticuloendothelial and monocyte/macrophage phagocytic systems before the injected antigen is able to activate antigen-specific B cells residing in the spleen or circulating as memory B cells in the periphery. In addition, antigen-antibody complexes are known to suppress ongoing immune responses by engaging inhibitory FcγRIIb receptors on B cells and, thus, prevent their activation and proliferation. This inhibition is part of a physiological response to terminate immune responses and prevent the development of autoimmune responses. Furthermore, in memory immune responses, the interfering but specific antibodies are likely to be produced by plasma cells in the bone marrow as a prominent site of long-term antibody production and thus the spleen may actually contain low numbers of antigen-specific B cells in case of mature antibody responses. Low overall numbers of specific antibody-producing B cells in donor spleens combined with poor de novo initiation and amplification of circulation-derived memory B cell responses due to pre-existing antibodies can be considered to be major reasons for the failure to increase the proportion of specific B cells in the final spleen cell suspension and, thus, reduce or compromise the chances of successful hybridoma generation.

The most common approach to avoid the negative effects of high titers of pre-existing antibodies is to wait until the target antigen-specific antibodies, including carrier-specific antibodies in case of antigen conjugates, have dropped significantly. Only then can the newly administered antigen, i.e. the final boost, result in significant antigen accumulation in the spleen to facilitate de novo B cell proliferation with cell kinetics compatible with successful hybridoma generation. Unfortunately, the time required for high antibody titers to sufficiently drop may take several weeks or even months. In many situations, however, the immunization of mice with high titres of pre-existing antibodies may still allow for the activation of a limited number antigen-specific B cells and thus result in the generation of a limited number of hybridomas.

Pre-existing antibodies are, thus, considered a major reason for the failure to induce extensive cell proliferation in preparation for hybridoma production. Therefore, it is the overall aim of the present invention to develop a method to avoid the negative effects of antibody interference and, thus, to increase the likelihood of successful hybridoma generation.

It was found that the specific cell proliferation in the spleen of naïve syngeneic non-human animals potentially increases after an adoptive cell transfer of spleen cells obtained from non-human animals previously immunized with the antigen of interest. Antigen-specific B cells are amplified in a recipient non-human animal to numbers often sufficiently high enough for successful hybridoma cell generation. The observed B cell proliferation in this approach is likely to be facilitated by the absence of interfering antibodies. Due to the transfer of cells between animals, the approach is called adoptive cell transfer.

Therefore, the present invention refers to a non-therapeutic method for the production of antigen-specific B cells by using adoptive cell transfer. The method comprises the following steps:

a) Primed B cells of immunized non-human animals are generated. The primed B cells are isolated from non-human animals previously immunized with the antigen of interest.

b) These primed B cells and the antigen of interest are administered to a naïve non-human animal in order to induce a humoral immune response against the antigen of interest.

c) Antigen-specific B cells are isolated from the recipient non-human animal.

The non-human animals are preferably mammals such as rodents, mice, rats, guinea pigs, rabbits, bovine, horses, dogs, cats, goats, sheep, and pigs. The animals are immunologically naïve animals with respect to the target antigen and are, thus, free of any antibodies against the antigen of interest. Non-human animals preferably used are mice or rats, with mice preferred over rats.

Primed B cells for the adoptive cell transfer are obtained from previously immunized non-human animals. After immunization according to standard protocols, host animal cells are harvested to obtain cell populations of primed B cells. Harvested cell populations can be isolated from any organ of immunized non-human animals and typically include the spleen, lymph nodes, the bone marrow, the omentum, Peyer's Patches or blood and/or peripheral blood mononuclear cells (PBMCs). The cells can be harvested from more than one source and pooled before processing. Preferably, spleen cells are preferred host animal cells. Especially spleen cells including B cells are used as primed B cells, the spleen cells are isolated from non-human animals previously immunized with the antigen of interest.

The cells to be transferred can be freshly isolated cells or resurrected from frozen cell stock of previously immunized non-human animals, i.e. the source of the cells to be transferred can be fresh or resurrected spleen cells. The immunization of the non-human animals to provide primed B cells is typically be performed according to standard protocols using the antigen of interest. That means the immunization can be performed by any method known in the art, such as, by one or more injections of the antigen of interest with or without any agent to enhance the immune response, such as complete or incomplete Freund's adjuvant or any other adjuvants, or by homogenizing a gel slice that contains the antigen. When a sufficient antibody titer is measured in the serum, immunized mice are euthanized and the cells to be used for transfer are isolated.

In an embodiment of the invention the primed B cells to be administered to the naïve recipient non-human animal are pre-treated by washing in serum-free cell culture medium and by lysis of the red blood cells. For example, the isolated cells are suspended in a total volume of 50 ml of serum-free cell culture medium and centrifuged. The resulting pellet is re-suspended in red blood cell lysis buffer for 1 min before adding serum-free medium to a total volume of 50 ml. An aliquot of the resulting cell suspension is taken for cell counting using preferably a haemocytometer. The red blood cell-free suspension of primed B cells is pelleted again by centrifugation and the pellet is finally re-suspended in physiological saline in a cell number-dependent volume suitable for cell transfer.

In an embodiment of the invention the primed B cells are administered to the naïve non-human animal prior to the administration of the antigen of interest to elicit a humoral immune response in the recipient animal. Although the antigen can be administered at any time following the cell transfer, the antigen injection will typically be performed at or shortly after the cell transfer i.e. within 1-2 h.

Such an approach is especially advantageous as the recipient animals do not have any specific antibodies against the antigen of interest at the time of the adoptive cell transfer. The antigen of interest given shortly after the transfer of primed B cells can directly activate transferred memory B cells while they are in transit especially to the spleen or after their arrival in the spleen. The spleen of the recipient non-human animal has been shown before to be one of the major organs for proliferating immune responses. Therefore, the extensive cell proliferation especially in the spleen will generate a significant pool of antigen-specific B cells in the spleen of the recipient non-human animal and can be used for hybridoma production.

The administration of primed B cells and of the antigen of interest to the naïve non-human animal can be performed by injection. After the injection, preferably into the peritoneal cavity, the transferred cells and the antigen drain into the spleen via the subdiafragmatic lymphatic system and the blood supply. Alternatively, other routes such as intravenous, subcutaneous, intralymphatic injection etc. can be used.

Normally, seven days after the transfer of the primed B cells and the antigen of interest, the extent of the developing immune response in the recipient animals are determined by measuring their antibody titers. Blood samples are taken and the serum antibody titers are determined by enzyme-linked immunosorbent assay (ELISA) or any other suitable immunoassay technique. If the antibody titers are considered to be high enough, a cell fusion can be carried out. If the titer is too low, animals can be boosted in antigen-dependent interval(s) until an adequate response is achieved, as determined by repeated blood sampling and titer measurements. Typically, after a resting period of 7-14 days following the last antigen boost the animals are ready for hybridoma generation.

The antigen of interest can be any substance to which an antibody can bind and includes but are not restricted to peptides or peptide conjugates, proteins or fragments thereof; carbohydrates; organic and inorganic molecules or haptens; receptors produced by animal cells, bacterial cells, and viruses; enzymes; agonists and antagonists of biological pathways; hormones; nucleic acids, lipids, nanoparticles and cytokines.

To be able to work as an antigen, low-molecular weight molecules (like haptens, peptides, amino acids, nucleic acids, certain toxins or active ingredients) should be coupled to immunogenic carrier proteins. Bovine thyroglobulin, ovalbumin and bovine serum albumin as well as the snail protein keyhole-limpet hemocyanin (KLH) are commonly used carrier proteins for antibody generation. Preferred antigens are proteins and peptide-conjugates. The preferred carrier proteins are bovine thyroglobulin (molecular weight: 660-690 kDa) or KLH (molecular weight: ca. 390 kDa).

The antigen-specific B cells generated in the recipient non-human animal can be isolated from any of the animal's organs. Typically, the antigen-specific B cells are obtained from the spleen, blood and/or any other primary (bone marrow) or secondary lymphoid organ such as lymph nodes, lymphatics, Peyer's Patches, omentum etc.

Hybridoma production is carried out according to standard protocols. In order to generate hybridoma cell lines producing monoclonal antibodies specific to the antigen of interest, the antigen-specific B cells are fused with myeloma cells. Hybridomas secreting specific monoclonal antibodies are identified, isolated and bulk grown either in vivo as ascites cultures or in vitro using a variety of tissue culture techniques.

Cell fusion, selection and cloning of a hybridoma cells is performed following standard protocols such as described for example in Peters, J. H. & Baumgarten, H. (Hersg.), Monoklonale Antikörper Herstellung und Characterisierung, 2. Auflage (1990), Springer Verlag or Harlow, E. & Lane, D., Antibodies A Laboratory Manual (1988), Cold Spring Harbor Laboratory.

Cell fusion is typically mediated by chemical fusogens such as polyethylene glycol but fusogenic viruses or electroporation are also possible. After cell fusion, the cells are suspended in selective growth medium composed of conventional cell growth media such as Dulbecco's Modified Eagle Medium (DMEM) or Roswell Park Memorial Institute (RPMI) medium each supplemented with HAT (hypoxanthine-aminopterin-thymine). The selective medium only allows hybrid cells to survive. The cell suspension is plated out in tissue culture plate wells that had been pre-coated the day before with peritoneal exudate cells as feeder cells. Instead of feeder cells, however, various commercially available additives can be used to improve the growth of the hybrids. Typically, after two weeks of cell culture, the culture supernatants of the growing hybridomas in each ELISA well are tested for the presence of antigen-specific antibodies using a variety of immunoassays such as ELISA, antigen microarrays of immunoblot techniques. All the cells of wells with specific antibodies are cloned by limiting dilution (single cell isolation by dilution) and the newly growing hybridomas derived from wells with a single cell colony (monoclonal) are retested for the presence of specific antibodies. The most productive and stable hybridoma is finally selected among all the antigen-positive hybridomas. Selected hybridomas are cryopreserved for long-term storage and specific antibodies are bulk grown using a variety of in vivo or in vitro techniques prior to antibody purification using various affinity chromatography techniques based among others on Protein A or G.

Hybridoma cells and monoclonal antibodies based on antigen-specific B cells produced according to the methods described above are also subject matter of the present invention.

The number of hybridoma cells generated using antigen-specific B cells produced according to the present invention can be much higher than those generated with the standard technique. The method of the present invention is a valuable additional technique for generating hybridoma cells against antigens with long-lasting antibody responses at very high concentrations. Furthermore, the method may proof especially valuable in situations where the standard technique of hybridoma production failed to generate any appropriate hybridomas but still allowed the activation of a low number of antigen-specific B cells that can then be amplified by the described invention. Moreover, any still available frozen host animal cells that were deposited as backup cells during a previous standard fusion can be resurrected and processed using the described invention.

EXAMPLES

Materials
BALB/c (8 to 12 weeks old) purchased from JANVIER LABS

Antigen 4, 5 and 6 being peptides coupled to bovine thyroglobulin, the antigen solutions are used in physiological saline at 1 mg/ml, (insoluble antigens are injected as suspension)
Freund's Complete Adjuvant, (CFA or FCA) and Freund's incomplete Adjuvant (IFA or FIA)
Red blood cell (RBC) lysis buffer
Myeloma cells SP 2/0-Ag-14 purchased from the DSMZ (Deutsche Sammlung von Mikroorganismen und Zellkulturen GmbH, Braunschweig, DE)

Example 1

Preparation of Antigen-Specific B Cells Using Adoptive Cell Transfer of Spleen Cells of Previously Immunized Mice and Administration of an Antigen of Interest to Naïve Mice The cell transfer is performed with freshly isolated spleen cells containing spleen cell populations including primed B cells from previously immunized mice or spleen cells resurrected from frozen spleen cell stocks, i.e. backup spleen cells previously isolated from immunized mice.

a) Immunization of mice with either antigen 4, 5 or 6 (see Table 1) for hybridoma generation using the standard protocol and the provision of primed B cells to be used for adoptive cell transfer.

For each antigen, 5 Mice are immunized with the antigen. The animals are given weekly injections of the antigen of interest emulsified in equal volumes of antigen and Freund's Adjuvants. Complete Freund's adjuvant is only used for the first immunization. Subsequent immunizations are performed with Incomplete Freund's adjuvant. The last immunization is performed in plain phosphate-buffered saline (PBS) or physiological saline. Alternative adjuvants such as Ribi, TiterMax, or Alum can also be used. Over the course of the standard 6-week immunization schedule, each mouse usually receives a total of four to five injections. The titer of the immune response is typically measured after the third injection and every subsequent immunization. Fresh spleen cells are isolated and aliquots are immediately used for hybridoma production using the standard technique or processed for adoptive cell transfer. Any additional surplus cells are frozen as backup cells for later processing if necessary.

b) Transfer of freshly prepared spleen cells into naïve mice and their subsequent immunization with either antigen 4 or 6 to generate hybridomas by the adoptive transfer method.

Immediately following the standard cell fusion, an aliquot of $150 \times 10^6$ cells of the same spleen cell population used in step (a) is washed in a 50-ml centrifuge tube by centrifugation in 50 ml of serum-free cell culture medium at 200×g for 8 min at room temperature. The cell pellet is re-suspended in 3.5 ml of red blood cell lysis buffer, and after 1 min of incubation serum-free culture medium is added, up to a final volume of 50 ml. An aliquot of 200 µl of the resulting cell suspension is taken for cell counting using a haemocytometer and the cell suspension is centrifuged again. The final cell pellet is re-suspended in physiological saline and the cell number is adjusted to $50 \times 10^6$/200 µl. A group of naïve mice (typically two mice) is injected intraperitoneally with 200 µl/animal of cell suspension, followed by 25-100 µg/animal of antigen 4 or 6, also in physiological saline, 1 hour later. The injections are carried out intraperitoneally. In order to monitor the developing immune response, the recipient mice are bled after 1 week and their serum antibody titers are determined by ELISA. Depending on the extent of the observed immune response, the mice can be boosted again in antigen-dependent interval(s) before finally using them for hybridoma production according to standard protocols. Typically, after a resting period of 7-14 days, the mice are ready to receiving their final boost for hybridoma generation. However, in case of insufficient serum antibody titers, the recipient mice can be rested (2-4 weeks) and boosted multiple times before measuring their serum antibody titers again.

c) Transfer of resurrected spleen cells into naïve mice and their subsequent immunization with antigen 5 to generate hybridomas by the adoptive transfer method using frozen spleen cell stock.

Frozen spleen cells are thawed and then prepared according to the procedure as described above under (b). For spleen cell resurrection, a cryo vial is retrieved from liquid nitrogen storage and the cells are rapidly thawed in a 37° C. water bath. The vial is transferred from the water bath to the laminar flow hood before its content is completely thawed. The right point in time for transfer of the cryo vial to the hood would be when the frozen cell pellet in the inverted cryo vial can be readily released from the bottom of the vial, i.e. drops down inside the vial after a forceful sudden downward movement. In the hood, the surface of the vial is disinfected with 70% isopropanol and the vial is opened. The cells in the still thawing cell pellet are step by step (0.5 ml volumes) re-suspended by multiply adding and withdrawing serum-free cell culture medium. The resulting 0.5 ml aliquots of thawing cells are transferred to 10 ml of serum-free cell culture medium and the cell suspension is then centrifuged at 200×g for 8 min at room temperature. The final cell pellet is re-suspended in 50 ml of serum-free cell culture medium and the cells are counted using a haemocytometer. After red blood cell lysis, the cells are processed for adoptive transfer as described above under b).

Example 2

Hybridoma and Monoclonal Antibody Bulk Production
Following hybridoma generation by adoptive transfer, monoclonal antibodies were bulk produced using standard in vitro tissue culture techniques and the antibodies were purified using standard affinity chromatography techniques before measuring the antibody concentrations spectrophotometrically.
The following production rates were determined:
Antigen 4: Hybridom a: 17.4 µg/ml IgG1/κ
  Hybridom b: 34.6 µg/ml IgG1/κ
  Hybridom c: 51.4 µg/ml IgG1/κ
Antigen 5: Hybridom a: 25.7 µg/ml IgG1/κ
  Hybridom b: 20.6 µg/ml IgG1/κ
Antigen 6: Hybridom a: 31.2 µg/ml IgG2b/κ
  Hybridom b: 64.0 µg/ml IgG1/κ

Table 1 compares the numbers of hybridomas generated by the standard technique and the adoptive cell transfer technique.

TABLE 1

Number of antigen-positive primary hybridomas according to the method of generation

| | Number of primary cultures generated through: | |
|---|---|---|
| | Standard technique | Adoptive cell transfer |
| Antigen No. 4 | 3 | 21 |
| Antigen No. 5 | 20 | 30 |
| Antigen No. 6 | 5 | 34 |

The invention claimed is:

1. A method for producing a hybridoma cell producing an antibody specific for an antigen of interest, comprising the steps of:
  producing antigen-specific B cells, wherein the antigen-specific B cells are produced by:
    a) providing primed B cells isolated from non-human animals which have been immunized with an antigen of interest;
    b) administration of the primed B cells and the antigen of interest to a nave non-human animal in order to induce a humoral immune response against the antigen of interest; and
    c) isolation of antigen-specific B cells from the non-human animal of step b); and
  fusing an antigen-specific B cell and a myeloma cell, resulting in a hybridoma cell producing an antibody specific for the antigen of interest.

2. The method according to claim 1, wherein the primed B cells are spleen cells including B cells isolated from non-human animals which have been previously immunized with the antigen of interest.

3. The method according to claim 1, wherein the primed B cells to be administered to the nave non-human animal are pre-treated by washing in serum-free cell culture medium and by lysis of the red blood cells.

4. The method according to claim 1, wherein the primed B cells to be administered to the naïve non-human animal are pre-treated by:
  washing the primed B cells in serum-free cell culture medium;
  pelleting the primed B cells by centrifugation;
  re-suspending the obtained cell pellet using red blood cell lysis buffer;
  adding serum-free culture medium;
  pelleting the primed B cells by centrifugation; and
  re-suspending the final cell pellet in physiological saline.

5. The method according to claim 1, wherein the primed B cells are administered to the naive non-human animal prior to the administration of the antigen of interest.

6. The method according to claim 1, wherein the administration of the primed B cells and/or of the antigen of interest is performed by injection, preferably by intraperitoneally, intravenously, subcutaneous or intralymphatic injection.

7. The method according to claim 1, wherein the developing immune response in the naïve non-human animal administered with the primed B cells and the antigen of interest is monitored, preferably the serum antibody titres in the blood are determined at predetermined time points.

8. The method according to claim 1, wherein the non-human animal administered with the primed B cells and the antigen of interest is boosted by additional administration of antigen of interest, preferably the time point for boosting is determined depending on the extent of the observed immune response.

9. The method according to claim 1, wherein the non-human animal to be administered with the primed B cells and the antigen of interest is a mammal, preferably selected from the group consisting of rodent, mouse, rat, guinea pig, rabbit, bovine, horse, dog, cat, goat, sheep, and pig, more preferably the non-human animal is a mouse or a rat.

10. The method according to claim 1, wherein the antigen of interest is one selected from the group consisting of peptides or peptide conjugates, proteins or fragments thereof; carbohydrates; organic and inorganic molecules; receptors produced recombinantly or by animal cells, bacterial cells, and viruses; enzymes; agonists and antagonists of biological pathways; hormones; nucleic acids, lipids, nanoparticles and cytokines.

11. The method according to claim 1, wherein the primed B cells and/or the B cells of the non-human animal administered with the primed B cells and the antigen of interest are isolated from spleen, blood or any other primary or secondary lymphoid organ.

12. A method for producing a monoclonal antibody, comprising the steps of:
    culturing the hybridoma cell produced by the method as defined in claim 1; and
    obtaining a monoclonal antibody against the antigen of interest from the culture of the hybridoma cell or the recombinant expression of the antibody genes.

* * * * *